United States Patent [19]

Tronconi

[11] Patent Number: 5,306,840
[45] Date of Patent: Apr. 26, 1994

[54] PROCESS FOR PREPARING PURE L-α-GLYCERYLPHOSPHORYL-D-MYOINOSITOL AND ITS SALTS

[75] Inventor: Giovanni Tronconi, Lodi, Italy

[73] Assignee: Euticals S.p.A., Milan, Italy

[21] Appl. No.: 916,978

[22] PCT Filed: Feb. 5, 1991

[86] PCT No.: PCT/EP91/00216
§ 371 Date: Aug. 5, 1992
§ 102(e) Date: Aug. 5, 1992

[87] PCT Pub. No.: WO91/12256
PCT Pub. Date: Aug. 22, 1991

[30] Foreign Application Priority Data

Feb. 9, 1990 [IT] Italy .................. 19323 A/90

[51] Int. Cl.$^5$ .................. C07F 9/10; C07F 9/117
[52] U.S. Cl. .................. 558/146; 558/150; 558/133; 558/177; 558/209; 558/110
[58] Field of Search .............. 558/150, 146, 133, 177, 558/209, 110

[56] References Cited

PUBLICATIONS

Lepage et al., Journal of the American Chem. Soc., vol. 82, pp. 3713–3715, (1969).
Hawthorne et al., Biochemistry Journal, vol. 71, pp. 195–200, (1959).

Primary Examiner—Marianne M. Cintins
Assistant Examiner—Margaret J. Page
Attorney, Agent, or Firm—Bucknam and Archer

[57] ABSTRACT

A process for preparing pure L-alpha-Glycerylphosphoryl-D-Myoinositol and its salts consists of a) preparing the crude Na+ or K+ salt of L-α-Glycerylphosphoryl-D-Myoinositol, passing an aqueous solution of the salt through an acid resin in H form whereby ion exchange occurs and the acid L-α-Glycerylphosphoryl-D-Myoinositol is eluted by washing the resin with water. Then the aqueous solution is passed through a basic resin whereby the L-α-Glycerylphosphoryl-D-Myoinositol is adsorbed on the resin as the anion. The resin is eluted first with a dilute solution of formic, acetic or propionic acid and then eluted with a more concentrated solution of the same acid. The preparation of severals salts is also described.

5 Claims, No Drawings

PROCESS FOR PREPARING PURE L-α-GLYCERYLPHOSPHORYL-D-MYOINOSITOL AND ITS SALTS

The present invention relates to a process for the preparation of L-α-glycerylphosphoryl-D-myoinositol and the salts thereof from crude or partially purified phosphatides.

BACKGROUND OF THE INVENTION

The preparation of L-α-glycerylphosphoryl-D-myoinositol (GPI) and the pharmaceutically acceptable salts thereof has not been described up to now.

Brown (J. Chem. Soc., 3774, 1959) and Brokeroff (J. Am. Chem. Soc., 2591, 1959) obtained L-α-glycerylphosphoryl-D-myoinositol as the cyclohexylammonium salt by acylating pure phosphatidylinositol (PI), a substance which is not commercially available and is obtained by means of a laborious process which cannot be carried out industrially.

Lapage (J. Am. Chem. Soc., 3713, 1960) obtained L-α-glycerylphosphoryl-D-myoinositol as the cyclohexylammonium salt by acylating maize crude phosphatides but, even though the purification is carried out on strong basic ion exchange resins with gradient elutions, the resulting cyclohexylammonium salt is not pure and repeated crystallizations must be performed in order to purify it.

The difficulty in obtaining pure L-α-glycerylphosphoryl-D-myoinositol starting from impure phosphatidylinositol (PI) was confirmed by Hawthorne (Biochem. J., 195, 1959), who isolated L-α-glycerylphosphoryl-D-myoinositol as the barium salt and obtained interesting results only by means of chromatography on strong basic ion exchange resins, with a gradient of a mixture of ammonium formate and sodium tetraborate and using pure phosphatidylinositol.

SUMMARY OF THE INVENTION

The present invention provides a simple and economical process for the preparation of the free acid L-α-glycerylphosphoryl-D-myoinositol as well as the salts thereof, of general formula (I)

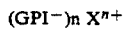

(GPI$^-$)$_n$ X$^{n+}$ wherein:
GPI is the glycerylphosphorylmyoinositol anion;
X is Na, Ca, Mg, Al, Zn, NH$_4$;
n is an integer from 1 to 3,
starting from crude or partially purified phosphatides. The process essentially consists of purifying crude L-α-glycerylphosphoryl-D-myoinositol by means of weak basic resins, using diluted aqueous solutions of an organic acid, such as formic acid, propionic or acetic acid. In this manner at first the impurities less acidic than L-α-glycerylphosphoryl-D-myoinositol, (L-α-glycerylphosphorylethanolamine (GPE), N-acyl GPE etc.) are removed by washing the resin with a diluted aqueous solution of the organic acid, without eluting L-α-glycerylphosphoryl-D-myoinositol, then the pure substance is recovered washing the resin with a more concentrated aqueous solution of the organic acid, without eluting the impurities more acidic than L-α-glycerylphosphoryl-D-myoinositol (L-α-glycerylphosphorylserine (GPS), glycerophosphoric acid, etc.), which can be eluted only when using saline aqueous solutions, but not with aqueous solutions of organic acids.

This simple purification cannot be achieved when using strong basic resins, since the complete elimination of L-α-glycerylphosphoryl-D-myoinositol is very laborious and above all since the substance cannot be recovered washing the resin with an aqueous solution of an organic acid: in fact, in this instance, saline aqueous solutions must be used, which involve the use of difficult chromatographic techniques to separate L-α-glycerylphosphoryl-D-myoinositol from acidic impurities.

The process according to the invention can be summarized as follows:

An alcoholic suspension (preferably in methanol or ethanol) of the mixtures of the crude or partially purified phospholipids is treated with alkali metal alkoxides (preferably sodium or potassium methoxide, ethoxide or tert-butoxide). After the salt formation is complete, the insoluble residue is filtered off and suspended again in the solvent, the suspension is adjusted to neutral or slightly acid pH (preferably from 4 to 7) with a mineral acid (hydrochloric, sulfuric, phosphoric acids) or with an organic acid (preferably formic, acetic, propionic acid), then it is filtered again. The solid containing crude L-α-glycerylphosphoryl-D-myoinositol Na or GPI K (depending on the alkoxide used is suspended in water (in a water/solid v/w ratio preferably from 1 to 2) and the suspension is added to an alcohol preferably methanol, ethanol or isopropanol in a v/v ratio, with respect to the used water, preferably from 1.5 to 3. The residue is filtered and washed with the same water-alcoholic mixture as the mixture used in the suspension. Alcohol is distilled off from the obtained water-alcoholic extract, then the aqueous solution is eluted first through a cationic resin in the acidic form, then through a weak basic resin, preferably in form of the hydroxide, acetate, formate. The resin is washed first with water, than with a diluted aqueous solution of an organic acid, preferably formic, acetic, propionic acid, in a concentration from 1 to 3% w/v, thereafter pure L-α-glycerylphosphoryl-D-myoinositol is recovered washing the resin with a solution of one of the above mentioned organic acids in a concentration from 5 to 10% w/v. The resulting solution is concentrated to a small volume under reduced pressure, preferably so as to obtain a L-α-glycerylphosphoryl-D-myoinositol concentration not above 10% w/v, then it is poured into acetone to obtain the substance in semi-solid form. The supernatant liquid is decanted, the residue is taken up into alcohol (preferably methanol, ethanol or isopropanol) and the solid acid L-α-glycerylphosphoryl-D-myoinositol is isolated.

The salts of formula (I) are obtained treating an aqueous solution of the obtained acid L-α-glycerylphosphoryl-D-myoinositol with a carbonate, a hydrogen carbonate, an oxide, a hydroxide of the metal corresponding to the desired salt, subsequently concentrating the solution to a small volume and finally precipitating with an alcohol (preferably methanol, ethanol or isopropanol).

EXAMPLE 1

Preparation of L-α-glycerylphosphoryl-D-myoinositol

A suspension of deoleated soy lecithin is used. Deoleated soy lecithin is a low cost commercial product consisting of a mixture of glycerophosphatides. The commercial product is prepared from crude soy lecithin by extraction with acetone and discarding the solution. Soy lecithin (1.22 kg) in methanol (4.5 l) containing sodium methoxide (60 g) is stirred at room temperature for 4 hours. The residue (equivalent to 600 g of dry residue) is filtered, washed with methanol (2×0.5 l), then suspended again in methanol (1.3 l) and added to glacial acetic acid to adjust the pH to about 4.5 (about 54 ml). The residue is filtered again, washed on the filter with methanol (2×300 ml), then dried at 40° C. under vacuum to obtain 400 g of dry product, containing about 10% L-α-glycerylphosphoryl-D-myoinositol Na.

The product is suspended in water (800 ml), 1.6 l of methanol is slowly added to the mixture, which is then stirred for about 30 minutes, then filtered, the residue on the filter is washed with 2×300 ml of a 2:1 methanol/water mixture. The water-alcoholic solutions are combined, methanol is distilled off under vacuum, the aqueous solution is treated twice with a mixture of decolourizing charcoal (10 g) and diatomaceous earth (10 g). The solution is filtered and eluted through 300 ml of Amberlite IR-120 H resin, by washing the resin with 600 ml of water. The resulting solution is passed through 200 ml of Amberlite R IR-93 OH resin, and the resin is washed first with water, then with a 3% w/v aqueous solution of acetic acid until the impurities are completely removed (checking by T.L.C.). The resin is then washed with a 8% w/v aqueous solution of acetic acid until complete recovery of L-α-glycerylphosphoryl-D-myoinositol. The solution is then concentrated under vacuum to small volume (about 300 ml), then poured into acetone (4 l) under stirring. The mixture is stirred at room temperature for 6 hours, then the liquid is decanted and the supernatant liquid is discarded. 600 ml of ethanol are added, the mixture is stirred for 5 hours at room temperature, then decanted and the supernatant liquid discarded. 300 ml of ethanol are further added, the mixture is stirred for 18 hours at room temperature, and the product is filtered, washed with ethanol and dried under vacuum at 30° C. on phosphoric anhydride, to obtain 31 g of L-α-glycerylphosphoryl-D-myoinositol.

$C_9H_{19}O_{11}P$ (M.W.=334.23).

Calculated: C=32.34%; H=5.73%; Found: C=32.19%; H=5.83%.

$^1$H-NMR (D$_2$O): ppm: 3.20–3.75 (6H, m); 3.75–4.10 (4H, m); 4.20 (1H, m);

Mass: 333=[M−1]; 259=[(M−1)—C$_3$H$_6$O$_2$]; 241=[(M−1)—C$_3$H$_6$O$_2$—H$_2$O]; 163=[C$_6$H$_{11}$O$_5$].

$\alpha_D$=−17.36 (c=2 in water).

m.p. 145°÷150° C. (dec.)

EXAMPLE 2

Preparation of GPI Cyclohexylammonium Salt

A solution of 15 g of pure acid GPI (obtained according to the process of example 1) in 150 ml of water is adjusted to pH 8 by addition of cyclohexylamine, then concentrated to small volume (about 30 ml) and diluted with ethanol (about 200 ml). The obtained precipitate, after filtration, is crystallized from ethanol and dried under vacuum at 40° C. over phosphoric anhydride. 14.5 g of GPI cyclohexylammonium salt are obtained.

$C_{15}H_{32}N\ O_{11}P$ (M.W.=433.4).

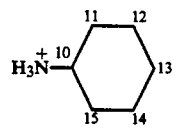
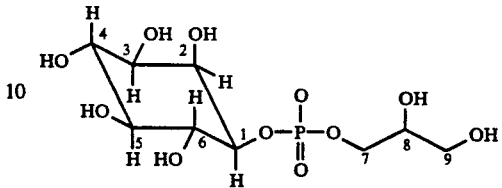

Calculated: C=41.57%; H=7.44%; N=3.23%; Found: C=41.67%; H=7.42%; N=3.20%.

$^1$H-NMR (D$_2$O) δ ppm: 1.00–1.20 (m; 4H; cyclohexyl); 1.33–1.48 (m; 2H; cyclohexyl); 1.48–1.60 (m; 2H; cyclohexyl); 1.67–1.80 (m; 2H; cyclohexyl); 2.80–3.00 (m; CH-10); 3.08 (dd; CH-5; J$_{5-4}$=J$_{5-6}$=9.3 Hz); 3.29 (dd; CH-3; J$_{3-2}$=2.70 Hz; J$_{3-4}$=9.30 Hz); 3.34–3.44 (m; CH-4+CH$_2$-9); 3.50 (dd; CH-6; J$_{6-5}$=J$_{6-1}$=9.30 Hz); 3.60–3.78 (m; CH-1+CH-8+CH$_2$-7); 4.00 (dd; CH-2; J$_{2-3}$=J$_{2-1}$=2.70); 4.60 (s; DHO);

$^{13}$C-NMR (D$_2$O) (fully decoupled): δ ppm: 26.19 (s; C-12+C-14); 26.68 (s; C-13); 32.72 (s; C-11+C-15); 52.74 (s; C-10); 64.43 (s; C-9); 68.70 (d; C-7; JC-O-P=5.72 Hz); 73.02 (d; C-8); 73.10 (s; C-3); 73.65 (m; C-2+C-6); 74.58 (s; C-4); ppm 76.32 (s, C-5); 78.60 (d, C-1; JC-O-P=5.9 Hz);

$\alpha_D$=−13.2 (c=2.09 in water)

EXAMPLE 3

Preparation of (GPI)$_2$Ca

A solution of 15 g of acid GPI (obtained according to the process of example 1) in 150 ml of water is adjusted to pH 5.5 by addition of calcium carbonate. The mixture is filtered, concentrated under vacuum to small volume (about 30 ml), then poured into 150 ml of methanol under stirring. Stirring is continued at room temperature for 1 hour, then the product is filtered, washing with methanol, and dried under vacuum at 40° C., to obtain 15 g of pure (GPI)$_2$Ca (a nearly non hygroscopic solid).

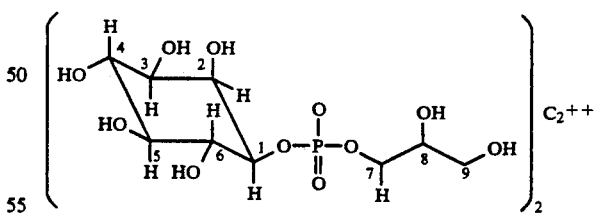

Calculated: C=30.60%; H=5.13%; Ca=5.67%; Found: C=30.56%; H=5.12%; Ca=5.58%.

$^1$H-NMR (D$_2$O) δ ppm: 3.37 (dd, CH-5; J$_{5-6}$=J$_{5-4}$=9.27 Hz); 3.58 (dd, CH-3; J$_{3-2}$=2.78 Hz; J$_{3-4}$=9.27 Hz); 3.65–3.75 (m; CH-4+CH$_2$-9); 3.79 (dd, CH-6; J$_{6-5}$=J$_{6-1}$=9.27 Hz); 3.90–4.10 (m; CH-1+CH-8+CH$_2$-7); 4.31 (dd, CH-2; J$_{2-3}$=J$_{2-1}$=2.78 z); 4.80 (s; DHO)

$^{13}$C-NMR (D$_2$O) (fully decoupled) δ ppm: 69.03 (s; C-9); 73.34 (d; C-7; J$_{C-O-P}$=5.6 Hz); 77.60 (d; C-8); 77.71 (s; C-3); 78.25 (m; C-2+C-6); 79.16 (s; C-4); 80.88 (s; C-5); 83.13 (d; C-1; JC-O-P=5.90 Hz)

$\alpha_D$=−15.46 (c=2.07 in water)

Following the same process as described in example 3, but using magnesium or barium carbonates, (GPI)$_2$Mg and (GPI)$_2$Ba are respectively obtained.

$C_{18}H_{36}O_{22}P_2Mg$ (M.W.=690.74).

Calculated: C=31.30%; H=5.25%; Mg=3.52%; Found: C=31.35%; H=5.21%; Ca=3.50%.

$a_D = -15.68$ (c=3.1 in water)

$C_{18}H_{36}O_{22}P_2Ba$ (M.W.=803.78).

Calculated: C=26.89%; H=4.51%; Found: C=26.74%; H=4.69%.

$a_D = -14.8$ (c=3.79 in water)

Following the same process as described in example 3, but using sodium, potassium or ammonium hydroxides, hydrogen carbonates or carbonates in such amounts as to adjust the pH of the solution from 4.5 to 5, GPI Na, GPI K and GPI NH are respectively obtained.

$C_9H_{18}O_{11}PNa$ (M.W. 356.21)

Calculated: C=30.35%; H=5.09%; Found: C=30.28%; H=5.18%.

$a_D = 14.9$ (c=3.3 in water)

$C_9H_{18}O_{11}PK$ (M.W. 363.32).

Calculated: C=29.75%; H=4.99% Found: C=29.84%; H=5.05%

$a_D = -15.1$ (c=2.3 in water)

$C_9H_{18}O_{11}PNH_4$ (M.W. 351.25).

Calculated: C=30.77%; H=6.31%; N=3.98%; Found: C=30.84%; H=6.45%; N=3.85%.

$a_D = -16.1$ (c=1.4 in water)

The above described salts can be obtained treating directly the aqueous solution of acid GPI of example 1, as described in example 3.

EXAMPLE 4

Preparation of (GPI)$_2$Mg from Partially Purified Phosphatidylinositol

A suspension of deoleated soy lecithin (1 kg) in methanol (2 l) is stirred at room temperature for 2 hours, then filtered. The residue is washed with methanol (800 ml), then suspended again in methanol and stirring at room temperature for one hour. The residue is filtered, washing with methanol (500 ml), then suspended in methanol (2.5 l) containing 40 g of sodium methoxide and treated as described in examples 1 and 3. 25 g of (GPI)$_2$Mg are obtained.

EXAMPLE 5

Preparation of (GPI)$_2$Ba from Organ Crude Phosphatides

A suspension of 500 g of phosphatides (containing about 10% PI, 10% PS, 30% PC, 30% PE) in methanol (3 l) containing 30 g of sodium methoxide is treated according to the process of examples 1 and 3. 9.6 g of (GPI)$_2$Ba are obtained. The process yields show significant changes as the PI content in crude phosphatides generally can vary markedly.

I claim:

1. A process for the production of pure L-α-glycerylphosphoryl-D-myoinositol (GPI) of formula I

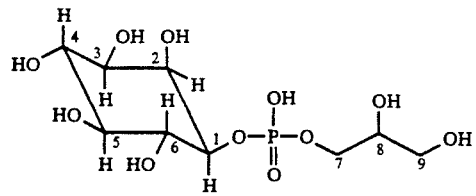

which consists of a) suspending a mixture of crude or partially purified glycerophosphatides which includes the glycerophosphatide of inositol in a solvent which is methanol or ethanol, to obtain a suspension, adding to said suspension sodium or potassium methoxide, ethoxide or t-butoxide to obtain the crude Na+ or K+ salt of L-α-glycerylphosphyoryl-D-myoinositol, in the form of a first insoluble residue;

b) filtering said first insoluble residue from step a) and suspending again said insoluble residue in the same solvent as in step a) to obtain a second suspension;

c) adjusting the pH of said second suspension from step b) to a value of 4-7 with a mineral acid or an organic acid to obtain a second insoluble residue and filtering said second insoluble residue containing the crude Na+ or K+ salt of L-α-glycerylphosphoryl-D-myoinositol;

d) suspending said second insoluble residue from step c) in water and adding a second solvent which is methanol, ethanol or isopropanol in a Vol/Vol ratio with respect to water of 1.5 to 3 to obtain a third suspension, filtering off the third insoluble residue and washing said third insoluble residue with a mixture of water and said second solvent to obtain an extract of water and said second solvent;

e) distilling off the solvent from said extract from step d) to obtain an aqueous solution;

f) passing said aqueous solution from step e) through a cation exchange resin in the H form whereby Na+ or K+ exchanges with the H+ of said resin and said L-α-glycerylphosphoryl-D-inositol of formula I is eluted by washing said resin with water to obtain a second aqueous solution;

g) passing said second aqueous solution from step f) through a weakly basic anion exchange resin in the OH form whereby said L-α-glycerylphosphoryl-D-inositol is adsorbed on said resin in the anion form due to the exchange of H for the OH of said resin;

h) washing said resin from step g) with water, then with a dilute solution of formic, acetic or propionic acid in the concentration of 1-3% by weight per volume of water to remove impurities less acidic than said L-α-glycerylphosphoryl-D-inositol which is adsorbed on said resin in the anion form;

i) eluting said resin from step h) with a 5-10% by weight solution of formic acid, acetic acid or propionic acid per volume of water to obtain an aqueous solution of pure GPI to obtain a third solution;

j) concentrating said third solution from step i), to obtain a concentrate wherein said GPI has a concentration not above 10% w/v, pouring the concentrated solution into acetone to obtain GPI as a semi-solid product, decanting the liquid, adding ethanol to said semi-solid product, to obtain a precipitate, filtering the precipitate and drying to obtain pure L-α-glycerylphosphoryl-D-myoinositol (GPI).

2. The process for the preparation of a pure salt of L-α-Glycerylphosphorylmyoinositol of formula $$(GPI^-)_n X^{n+}$$

wherein
GPI is the 1-α-glycerophosphoryl-D-myoinositol anion;
X is a cation selected from Na, Ca, Mg, Al, Zn and NH$_4$;
n is an integer from 1 to 3;
which consists of:
a) dissolving pure GPI, obtained according to claim 1, step j, in water to obtain a first aqueous solution;
b) adjusting the pH of said first aqueous solution from step a) with a base of the corresponding cation X to obtain a second aqueous solution;
c) concentrating said second aqueous solution from step b) to obtain a concentrate;
d) adding ethanol or methanol to said concentrated solution to obtain a precipitate and drying said precipitate.

3. The process according to claim 2, wherein in step b) said base is cyclohexylamine, the pH of said aqueous solution in step b) is adjusted to 8, said solution in step d) is diluted with ethanol and said pure salt is the cyclohexylammonium salt of L-α-glycerylphosphoryl-D-myoinositol.

4. The process according to claim 2, wherein said base in step b) is a member selected from the group consisting of calcium carbonate, magnesium carbonate, barium carbonate, sodium hydroxide, potassium hydroxide, ammonium hydroxide, sodium, potassium and ammonium bicarbonate, the pH of said aqueous solution in step b) is adjusted to 4.5–5 and said pure salt is the calcium, magnesium, barium, sodium, potassium or ammonium salt of L-α-glycerylphosphoryl-D-myoinositol.

5. The process according to claim 4, wherein said base in step b) is calcium carbonate, and said pure salt is the calcium salt of L-α-glycerylphosphoryl-D-myoinositol of the formula

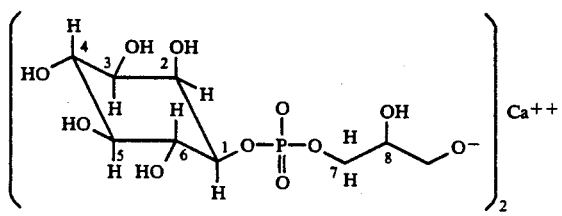

* * * * *